United States Patent
Wang et al.

(10) Patent No.: US 9,145,374 B2
(45) Date of Patent: Sep. 29, 2015

(54) SHIKIMATE PATHWAY INHIBITORS AND THE USE THEREOF

(71) Applicant: National Tsing Hua University, Hsinchu (TW)

(72) Inventors: Wen-Ching Wang, Hsinchu (TW); Shih-Ching Chou, Hsinchu (TW); Ming-Hua Hsu, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 27 days.

(21) Appl. No.: 14/151,815

(22) Filed: Jan. 10, 2014

(65) Prior Publication Data

US 2015/0141357 A1     May 21, 2015

Related U.S. Application Data

(60) Provisional application No. 61/906,598, filed on Nov. 20, 2013.

(51) Int. Cl.
| | |
|---|---|
| *C12Q 1/02* | (2006.01) |
| *C07D 239/62* | (2006.01) |
| *A61K 31/4164* | (2006.01) |
| *A61K 31/515* | (2006.01) |
| *A61K 31/7048* | (2006.01) |

(52) U.S. Cl.
CPC .......... *C07D 239/62* (2013.01); *A61K 31/4164* (2013.01); *A61K 31/515* (2013.01); *A61K 31/7048* (2013.01)

(58) Field of Classification Search
CPC ............. C07D 239/62; A61K 31/7048; A61K 31/515; A61K 31/4164
See application file for complete search history.

(56) References Cited

U.S. PATENT DOCUMENTS

2003/0229108 A1*  12/2003  De Belin et al. .............. 514/269

OTHER PUBLICATIONS

Motesharei et al. J. Am. Chem. Soc. (1998) 120: 7328-7336.*
Chandrashekhar et al. Der Pharma chimica (2011) 3(5): 329-333.*
Calamini et al. Nature Chem. Biol. (2012; published online Dec. 25, 2011) 8:185-196.*
Haldar et al. Bioorg. Med. Chem. Lett. (2008) 18: 2373-2376.*

* cited by examiner

*Primary Examiner* — Susan Hanley
(74) *Attorney, Agent, or Firm* — Hannah M. Tien

(57) ABSTRACT

The present invention relates to methods of inhibiting shikimate pathway, comprising administering to a subject a pharmaceutically acceptable composition comprising a compound having a formula:

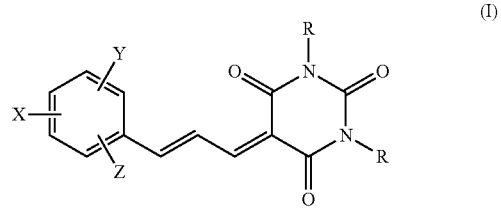

(I)

or pharmaceutically acceptable salts thereof. The present invention also provides a synergistic antibacterial composition containing compound

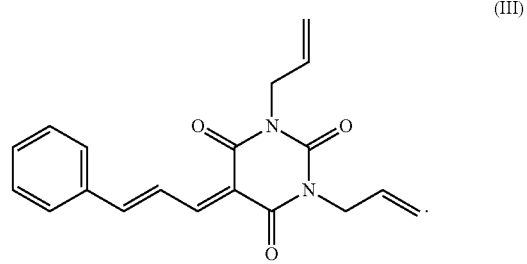

(III)

18 Claims, 7 Drawing Sheets

SHIKIMATE PATHWAY INHIBITORS AND THE USE THEREOF

FIELD OF THE INVENTION

The present invention provides methods and compounds of inhibiting shikimate pathway in a non-mammal host. The present invention also provides a synergistic antibacterial composition.

BACKGROUND OF THE INVENTION

*Helicobacter pylori*

A gram-negative spiral bacterium inhabits the gastric mucosa of humans, in which it may persist for a lifetime. The colonization of this unique ecological niche in approximately one-half of the human population makes it one of the most successful pathogens known to humankind. Enduring infection by *H. pylori* provokes active gastritis, alters gastric physiology, and may subsequently lead to peptic ulcer, atrophic gastritis, or even gastric adenocarcinoma. It is also recognized in the etiology of low-grade B-cell lymphoma.

*H. pylori* can be eradicated by the standard triple therapy comprised of a proton pump inhibitor and two antibiotic agents. The treatment of *H. pylori* infection using high-dosage antibiotics; however, has resulted in decreased efficacy. The infection proves to be difficult to cure; at least two high-dose antibiotics plus a proton pump inhibitor, twice daily for a 7- to 10-day period, is required to achieve high efficacy. Even more worrying, there is increasing emergence of resistant isolates that impede the cure rates, as seen for other bacteria including *Mycobacterium tuberculosis*. The development of novel drugs for resistant infections is thus needed for more effective control of these diseases in the future. Similarly, other resistant organisms including *Staphylococcus aureus* have become more and more difficult to cure. The need for new antibacterial therapies to overcome the problem of antibiotic resistance is therefore a major concern of healthcare professionals.

Current antibiotic agents are targeted towards a relatively small number of proteins, including cross-linking enzymes in the cell wall, ribosomal enzymes, and polymerases in DNA synthesis. One potential approach towards discovering new classes of inhibitors is to target crucial proteins in bacterial but not in mammals. The shikimate pathway, which involves seven sequential enzymatic steps in the conversion of erythrose 4-phosphate (E4P) and phosphoenolpyruvate (PEP) into chorismate for subsequent synthesis of aromatic compounds, is unique to microbial cells and parasites but absent in animals. Therefore, enzymes of this pathway are attractive targets for the development of nontoxic antimicrobial compounds, herbicides, and anti-parasitic agents. Indeed, the sixth-step enzyme, 5-enolpyruvylshikimate 3-phosphate (EPSP) synthase, has been exploited as a target with glyphosate, a well-known herbicide.

*Helicobacter pylori* (*H. pylori*) are microaerophilic spiral or curved-shaped gram-negative bacteria with 4 to 6 flagella. Human is the natural host of *H. pylori*, over 50% of population was infected by *H. pylori* around the world, and persistent infection of *H. pylori* is associated with intestinal disease including duodenal ulcers and gastric adenocarcinoma. The increasing problem of antibiotic resistance leads to treatment failure has become a concerning issue.

Shikimate Pathway

The shikimate pathway as shown in FIG. 1 links metabolism of carbohydrates to biosynthesis of aromatic compounds. In a sequence of seven metabolic steps, phosphoenolpyruvate and erythrose 4-phosphate are converted to chorismate, the precursor of the aromatic amino acids and many aromatic secondary metabolites. All pathway intermediates can also be considered branch point compounds that may serve as substrates for other metabolic pathways. The shikimate pathway only exists in plants, fungus and microorganisms, but not seen in animals which makes the pathway an attractive target for development of antimicrobial agents.

In microorganisms, the shikimate pathway is used to synthesize three proteinogenic aromatic amino acids, that is, tryptophan, phenylalanine, and tyrosine; the folate coenzimes; benzoid and naphtoid quinones; and a broad range of mostly aromatic, secondary metabolies, including some siderophores. Although the shikimate pathway branches at points, chorismate is the last common branch point for the above-mentioned compounds. Five distinct enzymes to prephenate, anthranilate, aminodeoxychorismate, isochorismate, and p-hydroxybezoate, respectively convert from chorismate. These metabolites comprise the first committed intermediates in the biosynthesis of Phe, Tyr, Trp, folate, menaquinone and the siderophore enterobactin, and ubiquinone, respectively. The synthesis of these precursors is in most cases highly regulated.

In plants, thousands of primary and secondary aromatic compounds, which play a role in plant growth, development, and defense, are synthesized via the shikimate pathway. The flow through the shikimate pathway accounts for up to 20% of the photosynthetically fixed carbon in plants, most of which is shuttled through Phe and Tyr to generate abundant phenylpropanoid metabolites. The complexes demand for aromatic secondary metabolites in specific cell types and in response to multiple environmental stimuli suggests that regulation of Phe and Tyr biosynthesis in plants may differ fundamentally from regulation observed in microorganisms.

In microorganisms, the shikimate pathway is regulated by feedback inhibition and by repression of the first enzyme 3 deoxy-D-arabino-heptulosonate-7-phosphate synthase (DAHPS). In higher plants, no physiological feedback inhibitor has been identified, suggesting that pathway regulation may occur exclusively at the genetic level. This difference between microorganisms and plants is reflected in the unusually large variation in the primary structures of the respective first enzymes. Several of the pathway enzymes occur in isoenzymic forms whose expression varies with environmental condition changes and, within the plant, from organ to organ.

SUMMARY OF THE INVENTION

Figure 1:
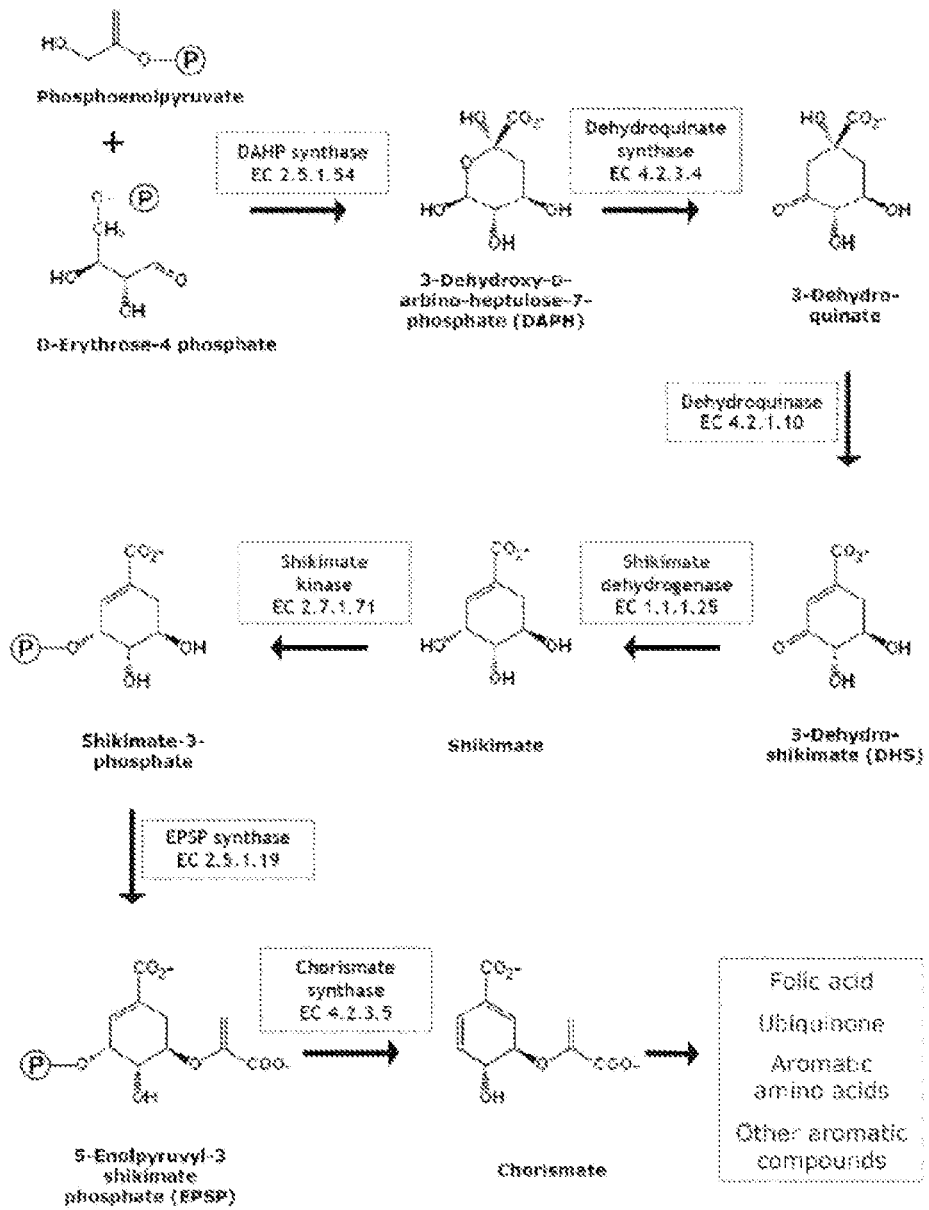
FIG. 1 illustrates the shikimate pathway.

The present invention relates to a method of inhibiting shikimate pathway in a non-mammal host, comprising administering to the host a therapeutically effective amount of a composition comprising a compound having the formula:

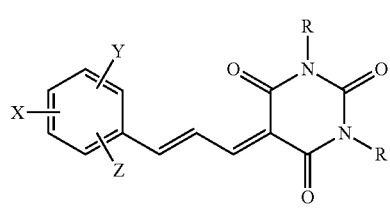

(I)

wherein X is H, $NO_2$, $OCH_3$, $SCH_3$ or benzamido; Y is H, $NO_2$, $OCH_3$ or $SCH_3$; Z is H, $NO_2$, $OCH_3$ or $SCH_3$; R is $C_{1-3}$ alkyl, $C_{2-4}$ alkenyl, dimethylphenyl or H; or salts thereof.

The present invention also relates to compound having the formula:

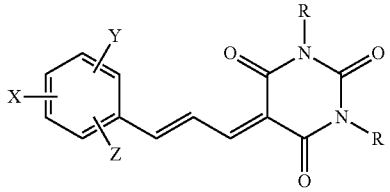

(II)

wherein X is H, $NO_2$, $OCH_3$, $SCH_3$ or benzamido, Y is H, $NO_2$, $OCH_3$ or $SCH_3$; Z is H, $NO_2$, $OCH_3$ or $SCH_3$; is $C_{1-3}$ alkyl or H; or salts thereof.

The present invention further relates to a synergistic antibacterial composition comprising a synergistic antibacterial effective amount of a combination of:

(A) compound

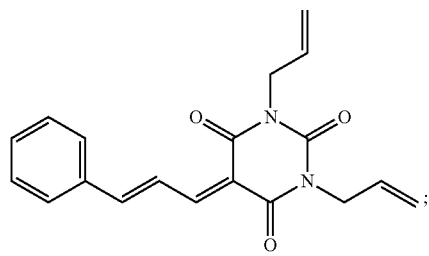

(III)

and
(B) metronidazole (MTR) or clarithromycin (CLR).

DETAILED DESCRIPTION OF THE INVENTION

The present invention provides a method of inhibiting shikimate pathway in a non-mammal host, comprising administering to the host a therapeutically effective amount of a composition comprising a compound having a formula:

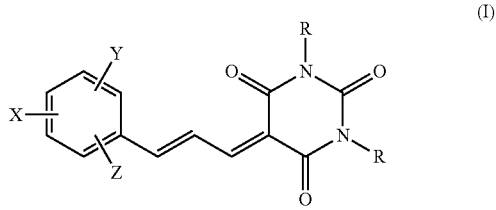

(I)

wherein X is H, $NO_2$, $OCH_3$, $SCH_3$ or benzamido; Y is H, $NO_2$, $OCH_3$ or $SCH_3$; Z is H, $NO_2$, $OCH_3$ or $SCH_3$; is $C_{1-3}$ alkyl, $C_{2-4}$ alkenyl, dimethylphenyl or H; or salts thereof.

In a preferred embodiment, X is H, Y is H, Z is H and R is H.

In another preferred embodiment, X is $C_3H_5$, Y is H, Z is H and R is H.

In another preferred embodiment, X is NH—$OC_7H_5$, Y is H, Z is H and R is H.

The present invention also provides a method of inhibiting the growth of non-mammal host comprising administrating to the subject an effective amount of a compound selected from the group consisting of:

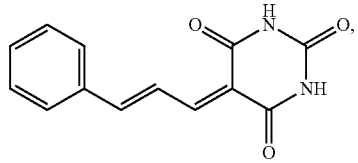

7a

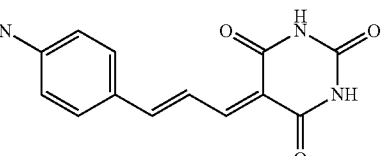

7b

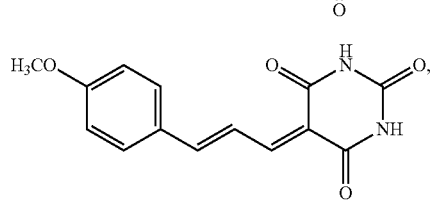

7d

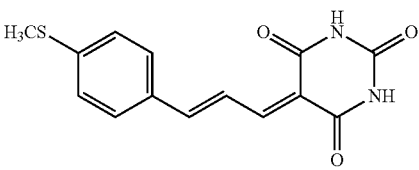

7e

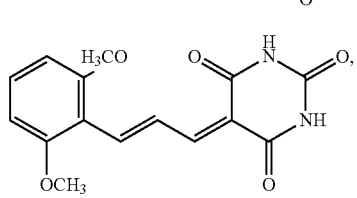

7h

-continued

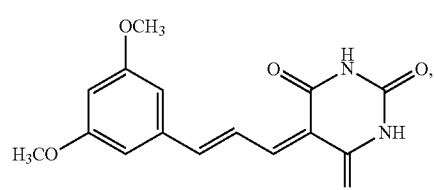
25a

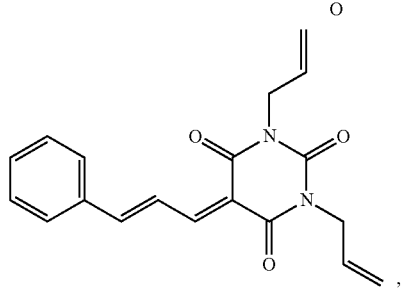
CB6942859

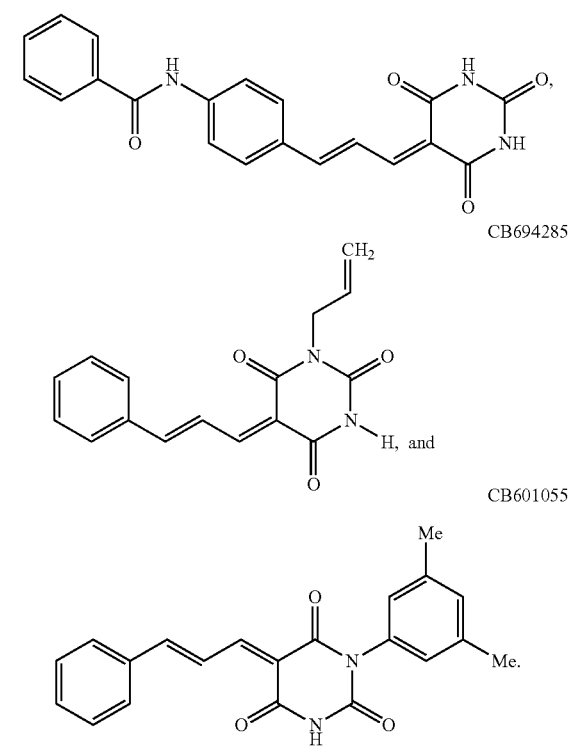
CB6010554

In a preferred embodiment, the non-mammal host includes plant, bacteria, fungi and parasite. Preferably, the bacteria is *Heliocobacter pylori* or *Mycobacterium tuberculosis*.

In a preferred embodiment, the compound inhibits the growth of *Heliocobacter pylori* and *Mycobacterium tuberculosis*.

The present invention relates to a compound of the invention having the formula:

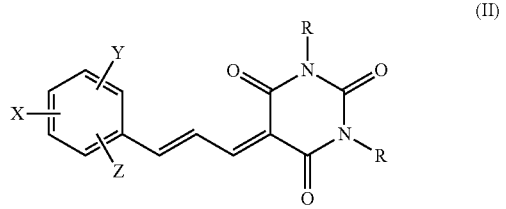
(II)

wherein X is H, $NO_2$, $OCH_3$, $SCH_3$ or benzamido; Y is H, $NO_2$, $OCH_3$ or $SCH_3$; Z is H, $NO_2$, $OCH_3$ or $SCH_3$; R is $C_{1-3}$ alkyl or H; or salts thereof.

The compound of the invention having the formula (II) inhibits the growth of *Heliocobacter pylori* and *Mycobacterium tuberculosis*.

The further preferred compound of the invention is

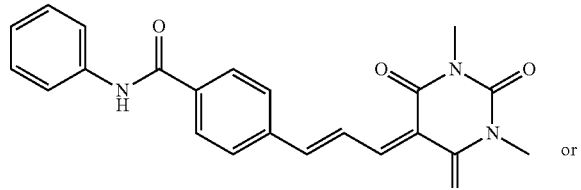
or

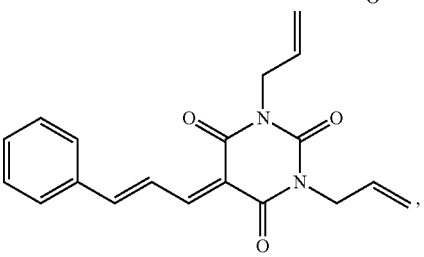

and serves as an inhibitor of shikimate dehydrogenase of the shikimate pathway in plant, bacteria, fungi or parasite. In bacteria particular in *Heliocobacter pylori* and *Mycobacterium tuberculosis*.

The present invention also relates to a synergistic antibacterial composition comprising a synergistic antibacterial effective amount of a combination of:

(A) compound

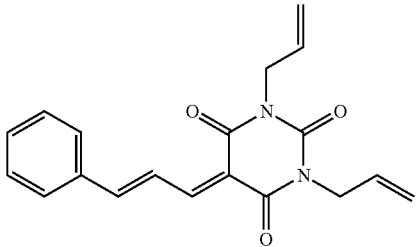 [SMILES: C=CCN1C(=O)C(=C/C=C/c2ccccc2)C(=O)N(CC=C)C1=O]
(III)

and;

(B) metronidazole (MTR) or clarithromycin (CLR).

The preferred synergistic antibacterial composition has a weight ratio of (A) and (B) is between 1:16 and 2:1.

In a preferred embodiment, synergistic anti-bacteria composition where dosage of

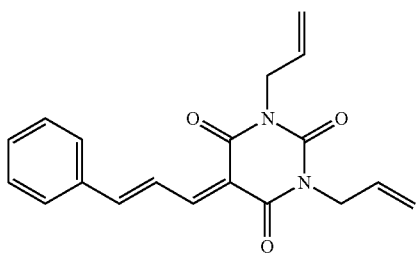 [SMILES: C=CCN1C(=O)C(=C/C=C/c2ccccc2)C(=O)N(CC=C)C1=O]

compound (III) is 2 mg/L and the dosage of metronidazole is 16 mg/L inhibit the growth of MTR-resistant strain.

In a preferred embodiment, synergistic anti-bacteria composition where dosage of

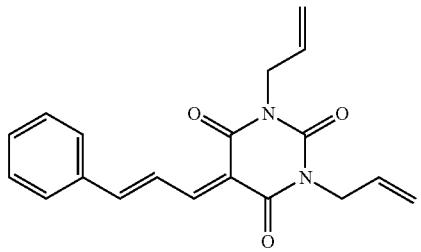

compound (III) is 2 mg/L and the dosage of clarithromycin is 4 mg/L inhibit the growth of CLR-resistant strain.

EXAMPLES

The examples below are non-limiting and are merely representative of various aspects and features of the present invention.

Example 1

Synthesis of Barbiturate Conjugated Derivatives and Bis-Barbiturate Conjugated Derivatives Methods and Materials To obtain barbiturate conjugated derivatives, Microwaves assistant Knoevanagel condensation was performed. The reaction can be done within 10 min assisted by microwaves to get desired compound for further biological assay.

To a mixture of barbituric acid (0.5 g, 3.9 mmol) and arylaldehyde (3.9 mmol, equiv.=1:1) in ethanol (5 mL) were set into a reaction vial tube. The mixture was heated in microwave reactor at 140° C. for 10 min. After the reaction cool down to room temperature, the mixture was poured into 15 mL water causing product precipitated and stirred for another 10 min. The precipitate was collected and washed by water twice to give corresponding compounds. 4, 5, 7, 8, 10, 11, 13 and 14 series compounds were synthesized through the general procedure to obtain high purity product with 70-92% yield. All synthesized compounds were confirmed by $^1$H NMR.

Preparation of (E)-N-(4-(3-(2,4,6-trioxotetrahydropyrimidin-5(2H)-ylidene) prop-1-en-1-yl)phenyl) benzamide To a mixture of compound 7b (1.0 equiv.) and 10% Pd/C (100 mg) in MeOH (50 mL) were set into a 150 mL flask connected with $H_2$ balloon. The reaction was stirred at room temperature under $H_2$ atmosphere for 21 to 24 hours, determined by TLC result. After the reaction finished. Pd/C powder was removed by filtration and solvent was removed by reduced pressure to get crude compound 15. Compound 15 was mixed with triethylamide (3.0 equiv.) and benzoyl chloride (2.5 equiv.) in dichloromethane (50 mL) in an oven-dried flask at 0° C. The reaction was stirred under $H_2$ atmosphere and back to room temperature for 6 hours. After the reaction finished, the mixture was extract by dichloromethane, and washed by water and brine twice. The product was purified with flash column chromatography using dichloromethane/methanol as eluent to get desired compound 17.

Preparation of N-phenyl-4-((2,4,6-trioxotetrahydropyrimidin-5(2H)-ylidene methyl)benzamide The starting material 18 (1.0 equiv.) was poured into sufonyl chloride (50 mL) and stir at room temperature for 8 hours under $N_2$ condition. After reaction, the solvent was removed by reduce pressure to obtain crude product 19. Compound 19 (1.0 equiv.) was mix with triethylamide (4.0 equiv.) in dichloromethane (50 mL) under $N_2$ condition. Aniline (20, 3.0 equiv.) was added by drops and the mixture stirred at room temperature for over-night. The solution was extract by dichloromethane and water, and washed by brine twice. Organic layer was dried over $MgSO_4$ and the product was purified with flash column chromatography using dichloromethane/methanol as eluent to obtain compound 21.

Preparation of 1,3-dimethyl-5-(4-(2-(piperidin-1-yl) ethoxy)benzylidene)pyrimidine-2,4,6(1H,3H,5H)-trione Prepared from compound 5h (2.60 g, 10 mmol) was dissolved in anhydrous DMF at room temperature. $K_2CO_3$ (3.92 g, 40 mmol) and chloroethylpiperidine (4.5 g, 30 mmol) were added and heated to 85° C. The mixture was stirred for 8 hours under $N_2$ environment. After reaction finished, catalyst was removed with filtration and the solvent was evaporated with reduced pressure. The crude mixture was extracted by dichloromethane and water. The organic layer was washed by water twice and dried over $MgSO_4$. Crude solution was purified with flash column using dichloromethane/methanol as eluent to get product 23.

Preparation of (E)-1,3-diallyl-5-(3-phenylallylidene) pyrimidine-2,4,6(1H,3H,5H)-trione Prepared from compound 7a (2.42 g, 10 mmaol, 1 equiv.) was dissolved in anhydrous DMF at room temperature. $K_7CO_3$ (3.92 g, 40 mmol) and allyl-bromide (3.63 g, 30 mmol) were added and heated to 85° C. The mixture was stirred for 8 hours under $N_2$ environment. After reaction, catalyst was removed with filtration and crude mixture was poured into water (100 mL) causing yellow solid precipitated. The solid product was collected by filter and purified with flash column using ethyl acetate/hexane as eluent to get product 25a.

Preparation of (E)-1,3-diallyl-5-(3-(4-methoxyphenyl)allylidene)pyrimidine-2,4,6(1H,3H,5H)-trione Prepared from compound 7b (2.72 g, 10 mmol, 1 equiv.) was dissolved in anhydrous DMF at room temperature. $K_2CO_3$ (3.92 g, 40 mmol, 3 equiv.) and allyl-bromide (3.63 g, 30 mmol, 3 equiv.) were added and heated to 85° C. The mixture was stirred for 8 hours under $N_2$ environment. After reaction finished, catalyst was removed with filtration and the solution was extract by ethyl acetate and water. The organic layer was washed twice and dried over $MgSO_4$. Crude solution was purified with flash column using ethyl acetate/hexane as eluent to get product 25b.

Results

To obtain various barbituric acid derivatives for further HpSDH inhibitor screening, more than 60 different barbiturate-conjugate compounds was designed and synthesized as potential inhibitors. Knoevenagel condensation was carried out with barbiturate and different aryl-aldehy in quantitative yield assisted by microwaves.

Figure 2:
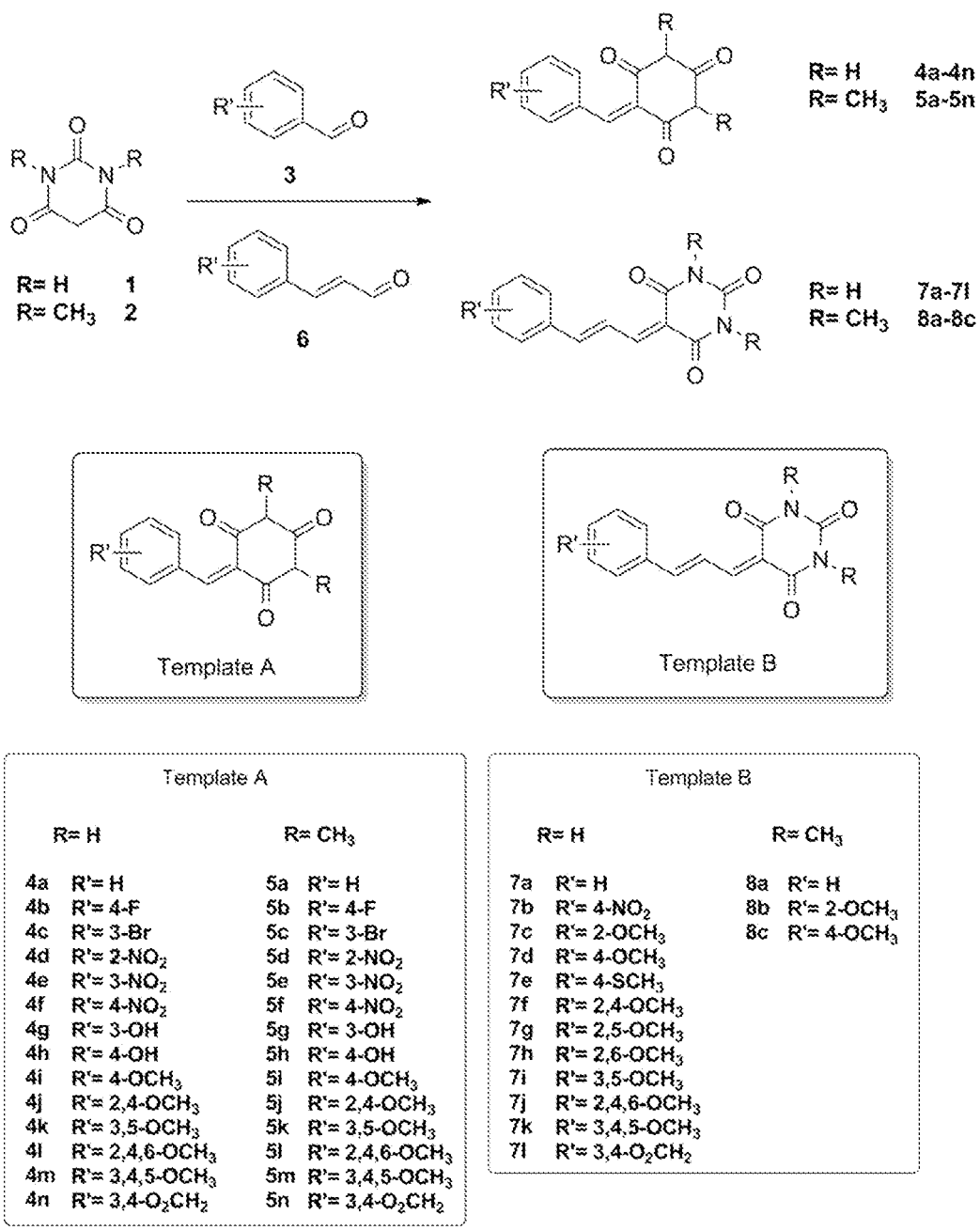
FIG. 2 illustrates synthesis of barbiturate conjugated derivatives 4a-n, 5a-n, 7a-l and 8a-c. By mixture of different and aryl-aldehyde and barbituric acid (1) or N,N-dimethyl substitute barbituric acid (2) in ethanol under microwave reactor at 140° C. for 10 minutes to give desired hybrid compound 4a-n and 5a-l for phenylaldehyde; 7a-n and 8a-d for conjugated phenylaldehyde with yield from 70-92%.

By mixture of different and aryl-aldehyde and barbituric acid (1) or N, N-dimethyl substitute barbituric acid (2) in ethanol under microwave reactor at 140° C. for 10 minutes to give desired hybrid compound 4a-n and 5a-l for phenylaldehyde; 7a-n and 8a-d for conjugated phenylaldehyde (FIG. 2) with yield from 70-92%. All compounds were purified by recrystallization to afford products with purity>95%.

Figure 3:
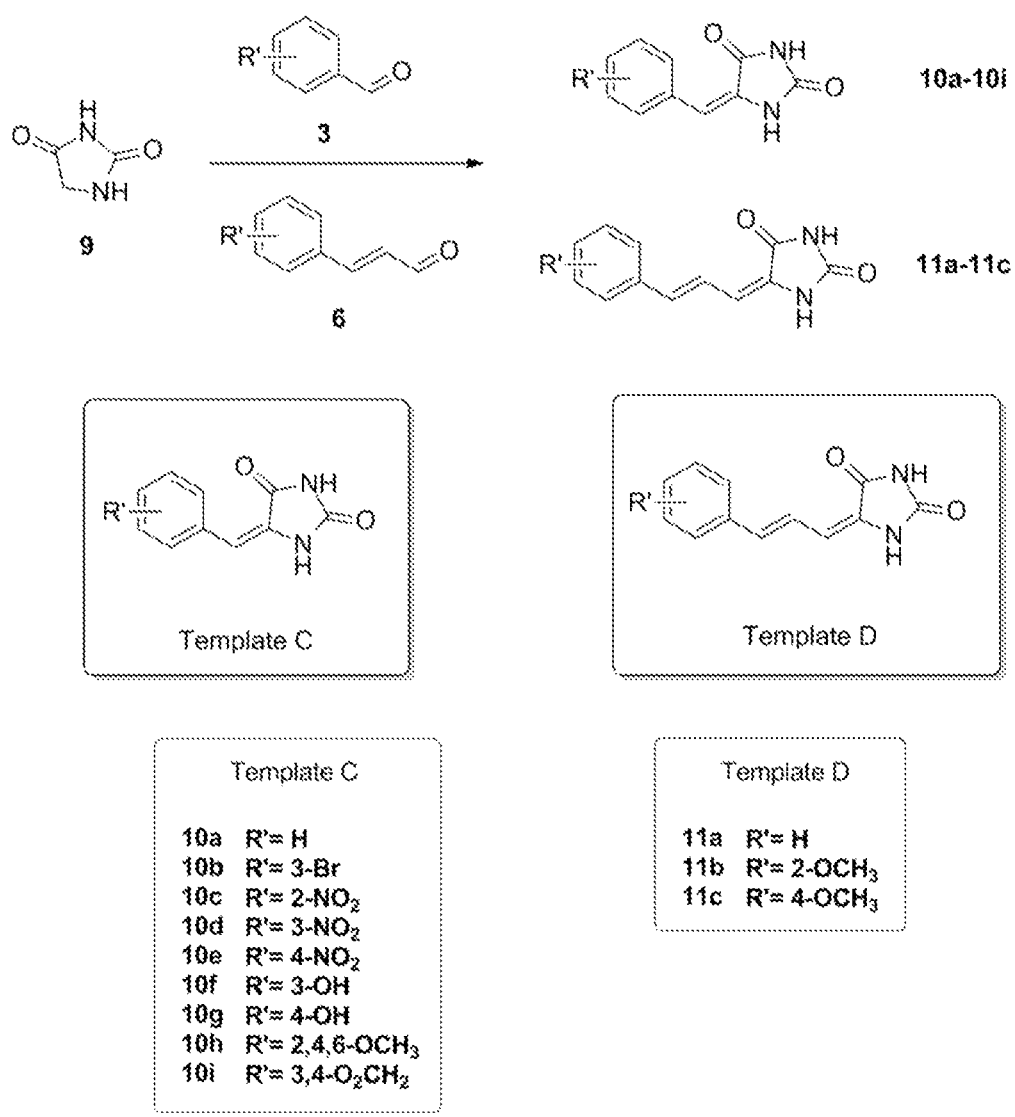
FIG. 3 illustrates synthesis of imidazolidine conjugated derivatives 10a-i and 11a-c. Knovevenagel condensation can also be achieved by arylaldehyde and hydantoin (imidazolidine-2,4-dione, 9), a five-member ring similar to barbituric acid, through the same general procedure with high yield.

Knovevenagel condensation can also be achieved by arylaidehyde and hydantoin (imidazolidine-2,4-dione, 9), a five-member ring similar to barbituric acid, through the same general procedure with high yield (FIG. 3).

Figure 4:
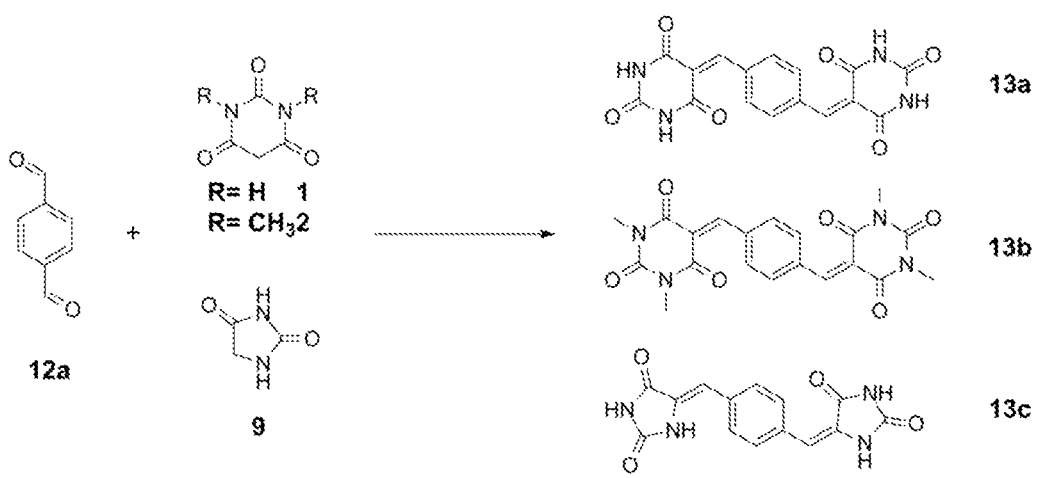
FIG. 4 illustrates synthesis of para his-barbiturate conjugated derivatives (13a-c).
Figure 5:
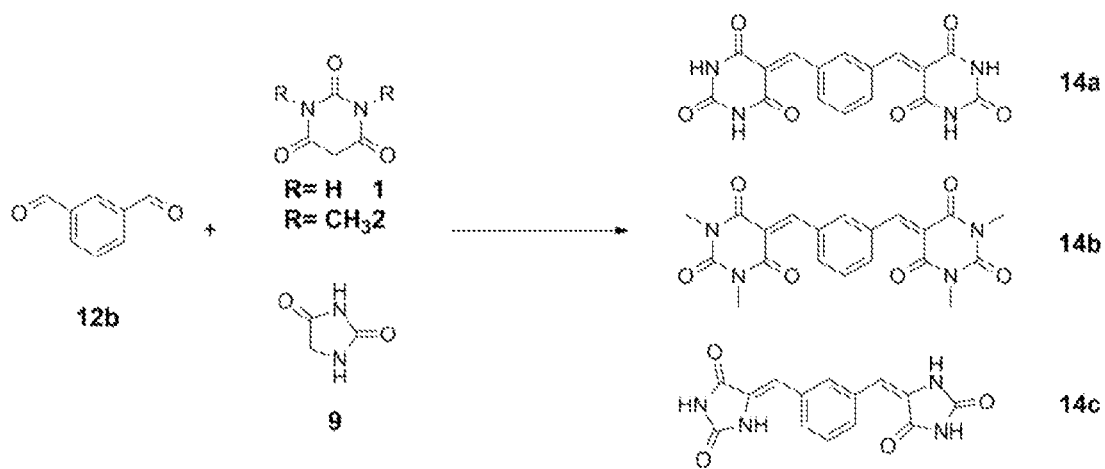
FIG. 5 illustrates synthesis of meta bis-barbiturate conjugated derivatives (14a-c).
Figure 6:
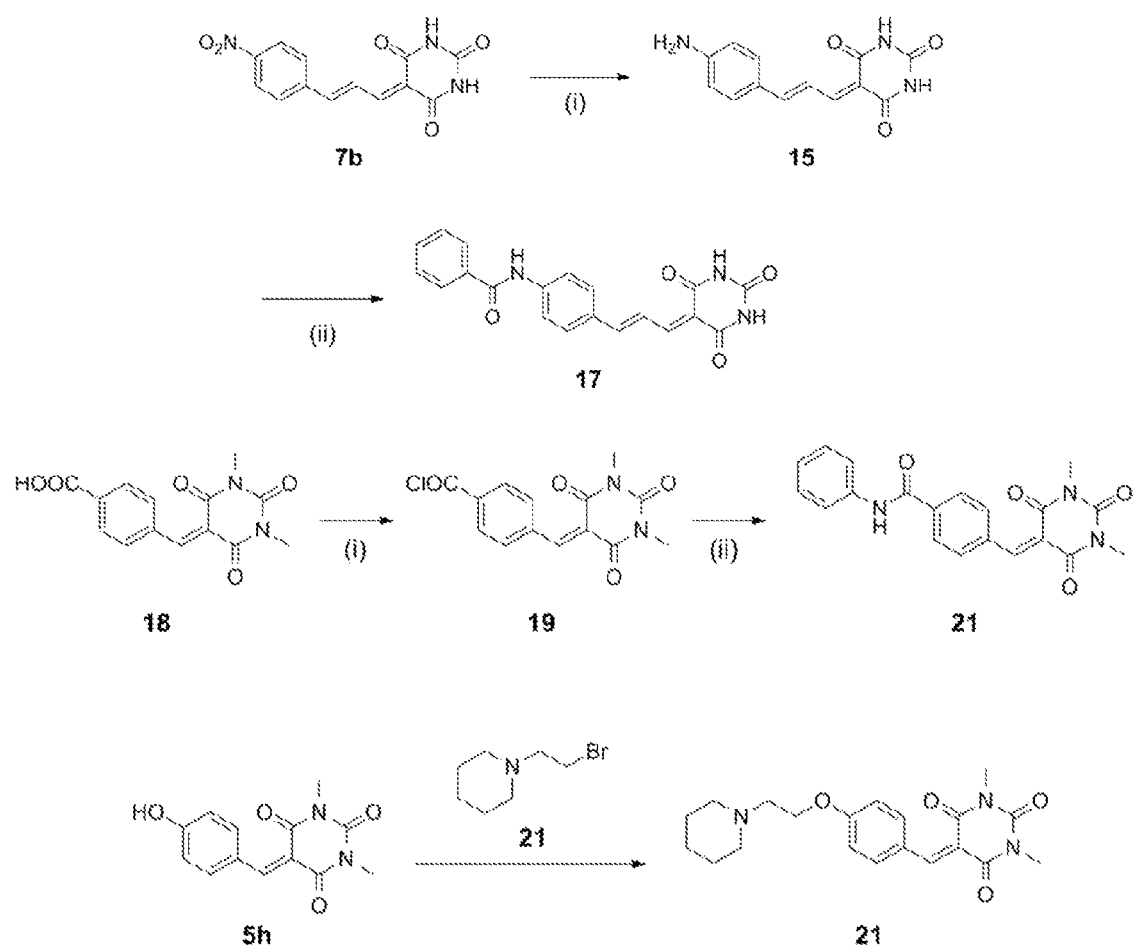
FIG. 6 illustrates synthesis series of bis-barbiturate conjugated derivatives (15-21).
Figure 7:
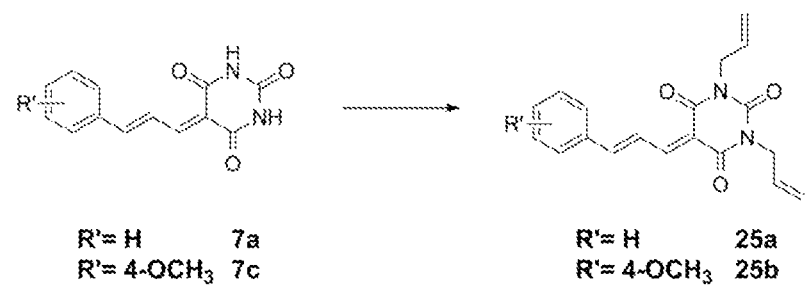
FIG. 7 illustrates synthesis of (E)-1,3-diallyl-5-(3-phenylallylidene)pyrimidine-2,4,6(1H,3H,5H)-trione and (E)-1,3-diallyl-5-(3-(4-methoxyphenyl)allylidene)pyrimidine-2,4,6(1H,3H,5H)-trione(25 a-b).

To further design of barbiturate-conjugated derivatives, series of double heads of barbiturate derivatives (Bis-barbiturate-conjugated derivatives) was designed through the general procedure as new derivatives to investigate biological activities and structure relationships. 1,4-benzenedicarboxaldehyde (12a) give para position of his-barbiturate derivatives (13a, 13b and 13c) (FIG. 4), and 1,3-benzenedicarboxaldehyde (12b) give meta position of bis-barbiturate derivatives (14a, 14b and 14c). (FIG. 5) Synthesis series of bis-barbiturate conjugated derivatives (15-21). (FIG. 6) Synthesis of (E)-1,3-diallyl-5-(3-phenylallylidene)pyrimidine-2,4,6(1H,3H,5H)-trione and (E)-1,3-diallyl-5-(3-(4-methoxyphenyl)allylidene)pyrimidine-2,4,6(1H,3H,5H)-trione (25 a-b). (FIG. 7)

Example 2

Antibacterial Activity Assays Toward *H. pylori*

To evaluate the anti-*H. pylori* activity, the minimum bactericidal concentration (MBC) value of compounds was determined. The MBC value of standard antibiotics, clarithromycine (CLR) and metronidazole (MTZ) were served as the positive control.

Materials and Methods

Wild Type (26695) and Clinical Isolate *H. pylori* Culture

Wild type (26695, as reference strain) was cultured on brucella broth agar plate containing 1% IsovialeX (Becton, Dickinson and Company, USA) and 10% sheep blood in microaerophilic environment (5% $O_2$, 10% $CO_2$, and 85% $N_2$), 37° C. Clinical strains (v574, v633, v1086, v1254, v1267, v1354 and v2311) were cultured on brucella broth agar plate containing 1% IsovialeX and 20%-30% sheep blood in microaerophilic environment (5% $O_2$, 10% $CO_2$, and 85% $N_2$), 37° C.

Minimum Bactericidal Concentration Assay (MBC Assay)

Wild type and selected clinical *H. pylori* strains was cultured for 24 to 36 hours and measured by Cell density meter, O.D. 680 at 0.87-0.9. *H. pylori* and selected compounds with serial concentration were mixed in Brucella-broth (BD) with 10% of FBS in 24-well plate, and total volume of each well was 300 μl, cultured under 37° C. with 180 rpm shaking. After incubated for 24 hours, 3 μl of each well was seeding on blood agar plate for another 48 hours culture. The minimum bactericidal concentration result was defined as the lowest concentration of the tested compound that completely inhibits the bacterial growth on the Brucella agar plate. The final concentration of DMSO in the assay was less than 5% to avoid any effect in the growth of *H. pylori* at this experiment.

*H. pylori* Shikimate Dehydrogenase (HpSDH) Expression and Purification

The recombinant HpSDH (aroE) was cloned in pET-28a plasmid and transformed into *E. coli* strain BL21 as expression host.

Results

Compounds 7 and 25-series showed good anti-bacterial activity to wild type (26695) and clinical isolated strains. The average MBC value toward wild type *H. pylori* was 8 mg/L recorded for 7b, 7d, 7e, 7g, 7h, 7i and 25a (Table 1.). The same result for other clinical isolate strains ranged from 4 mg/L, to 8 mg/L. Compounds 7b, 7d, 7h and 7i had the lowest MBC (4 mg/L) to v633 clinical isolate strain and 7g, 7h, 7i had good inhibit activity (4 mg/L) toward v1354 clinical isolate strain. In average, compounds 7d, 7e and 25a were three most potent inhibitors against *H. pylori*. In other way, benzyl barbiturate (Series 4 and 5), benzyl hydantoin (series 10 and 11) and his-barbiturate derivatives (Series 13 and 14) were shown no inhibition activity toward *H. pylori*. Compounds CB6010554 (10 mg/L) and CB6942859 (5 mg/L) also had good inhibit activity toward wild type strain.

TABLE 1

MBC value of synthesized compounds against *H. pylori*
MBC value of synthesized compounds against *H. pylori* (expressed as mg/L)

| | R | R' | W.T 26695 | Clinical isolated *H. pylori* strains | | | | | |
|---|---|---|---|---|---|---|---|---|---|
| | | | | v574 | v633 | v1086 | v1254 | v1267 | v1354 | v2311 |
| 7b | H | 4-$NO_2$ | 8.0 | 8.0 | 4.0 | 8.0 | 8.0 | 8.0 | 8.0 | 16.0 |
| 7c | H | 2-$OCH_3$ | 16.0 | 16.0 | 16.0 | 8.0 | 16.0 | 16.0 | 16.0 | 16.0 |
| 7d | H | 4-$OCH_3$ | 8.0 | 8.0 | 4.0 | 8.0 | 8.0 | 8.0 | 8.0 | 16.0 |
| 7e | H | 4-$SCH_3$ | 8.0 | 8.0 | 8.0 | 8.0 | 8.0 | 8.0 | 8.0 | 8.0 |
| 7g | H | 2,5-$OCH_3$ | 8.0 | 8.0 | 8.0 | 8.0 | 8.0 | 16.0 | 4.0 | 16.0 |
| 7h | H | 2,6-$OCH_3$ | 8.0 | 8.0 | 4.0 | 16.0 | 32.0 | 8.0 | 4.0 | 16.0 |
| 7i | H | 3,5-$OCH_3$ | 8.0 | 8.0 | 4.0 | 8.0 | 32.0 | 8.0 | 4.0 | 16.0 |
| 17 | H | p-NH—$OC_7H_5$ | 16.0 | 16.0 | 16.0 | 16.0 | 16.0 | 16.0 | 8.0 | 16.0 |
| 25a | $C_3H_5$ | H | 8.0 | 8.0 | 16.0 | 8.0 | 8.0 | 8.0 | 8.0 | 8.0 |
| CB6010554 | — | | 10.0 | — | — | — | — | — | — | — |
| CB6942859 | — | | 5.0 | — | — | — | — | — | — | — |

Example 3

Synergistic Effect of Compound 25a

TABLE 2

The synergistic effect of compound 25a in MBC test against *H. pylori*.

| | | 26695 Wild type | v1086 CLR-resistant strain | v574 MTR-resistant strain |
|---|---|---|---|---|
| Single treatment | MTR | <1.0 | <1.0 | 32.0 |
| | CLR | <1.0 | 8.0 | <1.0 |
| | 25a | 6.0 | 6.0 | 6.0 |

TABLE 2-continued

The synergistic effect of compound 25a in MBC test against *H. pylori*.

|  |  | 26695 Wild type | v1086 CLR-resistant strain | v574 MTR-resistant strain |
|---|---|---|---|---|
| Synergistic treatment | MTR + 25a | — | — | 16.0 + 2.0 |
|  | CLR + 25a | — | 4.0 + 2.0 | — |

Unit: mg/L
MTR: metronidazole
CLR: clarithromycin

Compound 25a inhibited bacterial strains in strain v574 (metronidazole resistant strains), compared to metronidazole which need 5 times of dosage to inhibit bacterial strain v574 (Table 2). In strain v1086 (Clarithromycin resistant strains), compound 25a inhibitory effect was similar to clarithromycin, which means compound 25a provides research development of inhibiting *H. pylori* drug templates that provide a basis for new antibacterial drug.

Synergy effect shown in Table 2, compound 25a and MTR reduced clarithromycin dosage and achieved the inhibition of bacterial strains CLR and MTR resistant strain. MTR against resistant strains, dosage of MTR 16 mg/L cannot suppressed the growth of v574 strain, but at the same time by adding compound 25a 2 mg/L complete suppression effect was achieved. Dosage of CLR 4 mg/L cannot completely inhibit the growth of resistant strains v1086, but while adding compound 25a 2 mg/L, complete suppression effect was achieved.

Example 4

Inhibition Activity Assay Toward HpSDH

Methods and Materials

Relative HpSDH activity calculations were based on the initial velocity that absorbance at the 5 to 10% of the time when reaction absorbance reached the maximum level. The variable slope of this time interval represented the reaction rate of HpSDH at various concentration of compound and normalized with the negative control HpSDH (without inhibitor) which represented 100% activity.

To evaluate structure activity relationship (SAR), all the synthesized compounds in SDH inhibition activity on wild type HpSDH recombinant protein was evaluated. All the datas of effective compounds were expressed as $IC_{50}$ value after treated with different compounds. In primary screening, using 100 μM as priminary screening concentration to evaluate all synthesized compounds. It was found that 4 and 5 series compounds did not show inhibition activity while 7, 8 and 25 series compounds exhibited good inhibition activity toward HpSDH. Compounds 7a, 7c, 7d, 7e, 7h, 7i, 17 and 25a are more effective inhibitors. The $IC_{50}$ of these compounds are 7a, $IC_{50}$=32.7 μM; 7c, $IC_{50}$=33.7 μM; 7d, $IC_{50}$=35.1 μM; 7e, $IC_{50}$=22.0 μM; 7i, $IC_{50}$=20.3 μM; 17, $IC_{50}$=16.1 μM and 25a, $IC_{50}$=11.4 μM.

When replacing the barbituric acid with hydantoin (10 and 11 series compounds) shown no inhibition activity. Bis-barbiturate (13 and 14 series) also did not show any inhibition toward HpSDH.

Example 5

Enzymatic Kinetics of Effective Compounds Toward HpSDH

Materials and Methods

HpSDH Enzymatic Activity Assays

The enzymatic activity of HpSDH was measured in the direction of reduction of $NADP^+$ to NADPH in the present of shikimic acid at 340 nm absorbance and conducted in 96-well plate ELISA reader. The final concentration of shikimic acid and $NADP^+$ were 2 mM, and the final protein concentration was 100 nM. Shikimic acid was added by injector needle equipped in ELISA reader to ensure the measurements were made at the same time spacing. NADPH would accumulate along with reaction, and the absorbance at 340 nm would be measured in every cycle of HpSDH reaction.

From the previous result, 7e, 7i, 17 and 25a were more effective inhibitors toward 26695-HpSDH with lower $IC_{50}$ values ranged from 11 μM to 22 μM. To study the inhibition mode of these compounds and inhibition type to shikimic acid and $NADP^+$, different concentrations of inhibitors and graded concentrations of substrates by activity assay was examined.

Inhibition type of selected inhibitors 7e, 7i, 17 and 25a showed competitive inhibition toward $NADP^+$ with Ki value of compound 7e is 2.67 μM; The Ki value of compound 7i is 3.81 μM; The Ki value of compound 17 is 6.93 μM; The Ki value of compound 25a is 2.01 μM, but these inhibitors showed non-competitive or uncompetitive toward shikimic acid instead.

Example 6

Molecule Docking

Materials and Methods

Docking Model Generation

Molecular docking of effective compounds for structure-activity relationship analysis of 26695-HpSDH was generated by Discovery Studio 3.5 (accelrys, USA). In first step of molecular docking, enzyme cavity structure and compounds (conversed to 3D conformation) were input into Discovery Studio and screen for possible binding site by LibDock program. LibDock scores indicated the ranking of predicted possible binding sites. Top 10 candidates will be selected for molecular dynamics analysis and refinement by CDocker to generate possible pose models. The results also ranked by binding energy, and the top 1 candidate which has the lowest binding energy was used as final docking model.

Compounds 7e and 7i, also shown hydrogen bonds and cation-π interaction with amino acid in the cavity. Compound 7e shown an H-bond interaction with Glu70 and a cation-π interaction with Lys69; Compound 7i form H-bonds with Glu70 and Thr65, and a cation-π interaction with Lys69. Compound 17 interact with the cavity amino acid through H-bonds with shikimate and Leu208, and form a cation-π interaction with Arg71; Compound 25a from H-bond with Ser129 and a cation-π interaction with Lys69.

What is claimed is:

1. A method of inhibiting shikimate pathway in a non-mammal host, comprising administering to the host a therapeutically effective amount of a composition comprising a compound having the formula (I)

wherein X is H, $NO_2$, $OCH_3$, $SCH_3$ or benzamido;
Y is H, $NO_2$, $OCH_3$ or $SCH_3$;
Z is H, $NO_2$, $OCH_3$ or $SCH_3$;
R is $C_{1-3}$ alkyl, $C_{2-4}$ alkenyl, dimethylphenyl or H;
or salts thereof.

2. The method of claim 1, wherein the non-mammal host is a plant, bacteria, fungi or parasite.

3. The method of claim 2, wherein bacteria is *Helicobacter pylori* or *Mycobacterium tuberculosis*.

4. The method of claim 1, wherein X is H, Y is H, Z is H and R is H.

5. The method of claim 1, wherein X is C₃H₅, Y is H, Z is H and R is H.

6. The method of claim 1, wherein X is NH—OC₇H₅, Y is H, Z is H and R is H.

7. The method of claim 1, wherein the compound is:

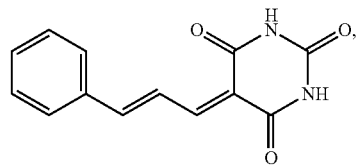
7a

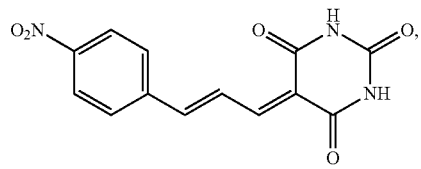
7b

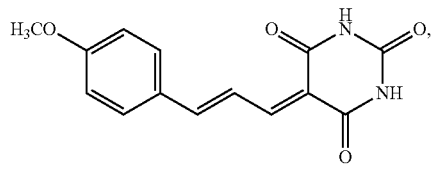
7d

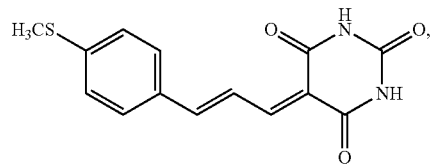
7e

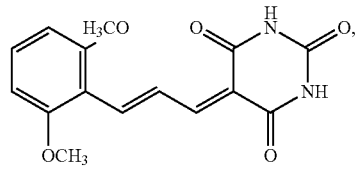
7h

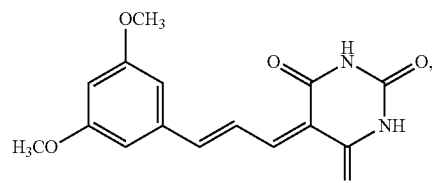
7i

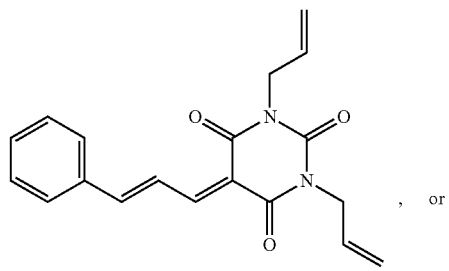
25a

, or

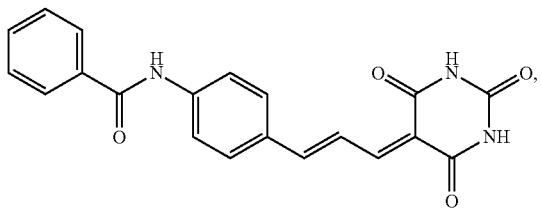
17

CB6942859

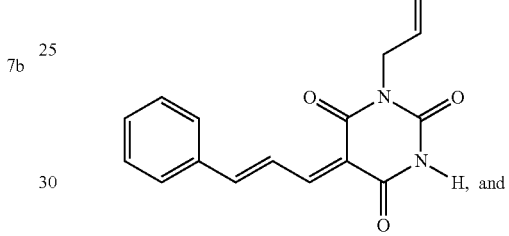
H, and

CB6010554

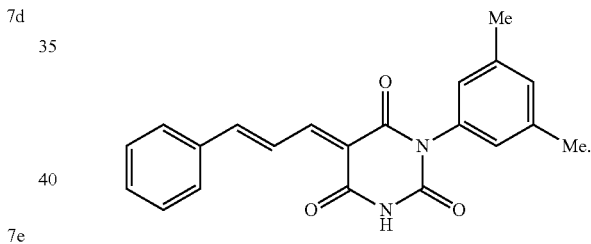

8. The method of claim 1, wherein the compound serves as an inhibitor of shikimate dehydrogenase of the shikimate pathway in plant, bacteria, fungi or parasite.

9. The method of claim 1, wherein the compound inhibits the growth of *Helicobacter pylori* and *Mycobacterium tuberculosis*.

10. A compound having the formula

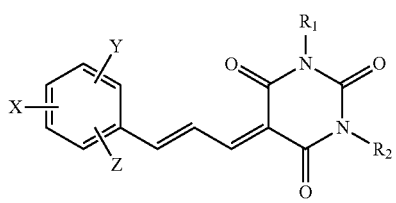
(II)

wherein
(1) X is H, NO₂, OCH₃, SCH₃ or benzamido,
Y is H, NO₂, OCH₃ or SCH₃,
Z is H, NO₂, OCH₃ or SCH₃,
$R_1$ is $C_{1-3}$ alkyl, $C_{2-4}$ alkenyl, or dimethylphenyl,
R2 is $C_{2-3}$ alkyl, $C_{2-4}$ alkenyl, dimethylphenyl or H; or
(2) X is NO₂, OCH₃, SCH₃ or benzamido,
Y is H, NO₂, OCH₃ or SCH₃,
Z is H, NO₂, OCH₃ or SCH₃, R1 is $C_1$ alkyl,
R2 is $C_1$ alkyl; or
(3) X is $NO_2$, $OCH_3$, $SCH_3$ or benzamido,
 Y is H, $NO_2$, $OCH_3$ or $SCH_3$,
 Z is $NO_2$, $OCH_3$ or $SCH_3$,
 R1 is H,
 R2 is H; or
(4) X is $SCH_3$ or benzamido,
 Y is H,
 Z is H,
 R1 is H,
 R2 is H;

or salts thereof.

11. The compound of claim 10, wherein the compound serves as an inhibitor of shikimate dehydrogenase of the shikimate pathway in plant, bacteria, fungi or parasite.

12. The compound of claim 10, wherein the compound inhibits the growth of *Helicobacter pylori* and *Mycobacterium tuberculosis*.

13. A synergistic antibacterial composition comprising a synergistic antibacterial effective amount of a combination of:

(A) a compound of formula (III)

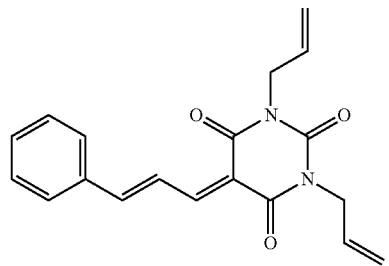 [SMILES: C=CCN1C(=O)C(=C/C=C/c2ccccc2)C(=O)N(CC=C)C1=O]

and;

(B) metronidazole (MTR) or clarithromycin (CLR).

14. The composition of claim 13, wherein the weight ratio of (A):(B) is between 1:16 and 2:1.

15. The composition of claim 13, wherein the dosage of compound (III) is 2 mg/L and the dosage of metronidazole is 16 mg/L.

16. The composition of claim 15, which inhibits the growth of MTR-resistant strain.

17. The composition of claim 13, wherein the dosage of compound (III) is 2 mg/L and the dosage of clarithromycin is 4 mg/L.

18. The composition of claim 17, which inhibits the growth of CLR-resistant strain.

* * * * *